United States Patent [19]

Karami

[11] 4,405,310
[45] Sep. 20, 1983

[54] SANITARY NAPKIN ASSEMBLY

[75] Inventor: Hamzeh Karami, Tilff, Belgium

[73] Assignee: Colgate-Palmolive Company, New York, N.Y.

[21] Appl. No.: 315,383

[22] Filed: Oct. 27, 1981

[51] Int. Cl.³ .............................................. A61F 13/16
[52] U.S. Cl. ................................... 604/383; 604/389
[58] Field of Search .............. 128/284, 286, 287, 288, 128/290 R; 604/372, 373, 378, 383, 385, 389–390

[56] References Cited

U.S. PATENT DOCUMENTS

| | | | |
|---|---|---|---|
| 3,367,334 | 2/1968 | Testa | 128/DIG. 30 |
| 3,570,492 | 3/1971 | Bettencourt | 128/290 R |
| 3,672,371 | 6/1972 | Roeder | 128/DIG. 30 |
| 4,195,634 | 4/1980 | DiSalvo et al. | 128/DIG. 30 |

Primary Examiner—C. Fred Rosenbaum
Attorney, Agent, or Firm—Norman Blumenkopf; Murray M. Grill; Herbert S. Sylvester

[57] ABSTRACT

A sanitary napkin assembly comprising a pair of absorbent pads with a mounting sheet or strip therebetween. The bottom absorbent pad is optionally used on days of severe menstration and is attached to the upper absorbent pad by adhesive on the mounting sheet or strips. The mounting sheet has a plurality of openings therein through which fluid can pass. When only one pad is used, the mounting sheet or strips has a peelable waterproof thin sheet adhesively secured thereto.

3 Claims, 3 Drawing Figures

SANITARY NAPKIN ASSEMBLY

BACKGROUND OF THE INVENTION

1. Field of the Invention

This invention relates to sanitary napkins and more particularly to a sanitary napkin assembly for facilitating protection against menstral flow whether light or severe.

2. Description of the Prior Art

At the present time available sanitary napkins are of three types. One heavy duty and quite expensive sanitary napkin is adapted for use during periods of heavy menstral flow. A second less expensive sanitary napkin is available for use during days when the menstral flow is lighter. A third form of napkin is for everyday use when there is only very light discharge, if any.

In order to provide for the three aforesaid conditions, consumers must maintain a supply of all three types of sanitary napkins which requires a monetary outlay and considerable storage.

The present invention overcomes the aforesaid difficulties of prior art napkins by providing a sanitary napkin assembly adapted for all three requiredments of usage.

SUMMARY OF THE INVENTION

In accordance with the concepts of the present invention a sanitary napkin assembly is provided utilizing one or more absorbent pads. On heavy menstral days, at least two absorbent pads are employed with a lower absorbent pad being secured to the upper pad by adhesive on suitable mounting means. A peelable waterproof strip is attached to the mounting means of each absorbent pad and forms a waterproof seal for the lowest absorbent pad.

The mounting means may be a plurality of strips or a sheet with a plurality of openings therethrough.

DETAILED DESCRIPTION OF THE INVENTION

Figure 1:
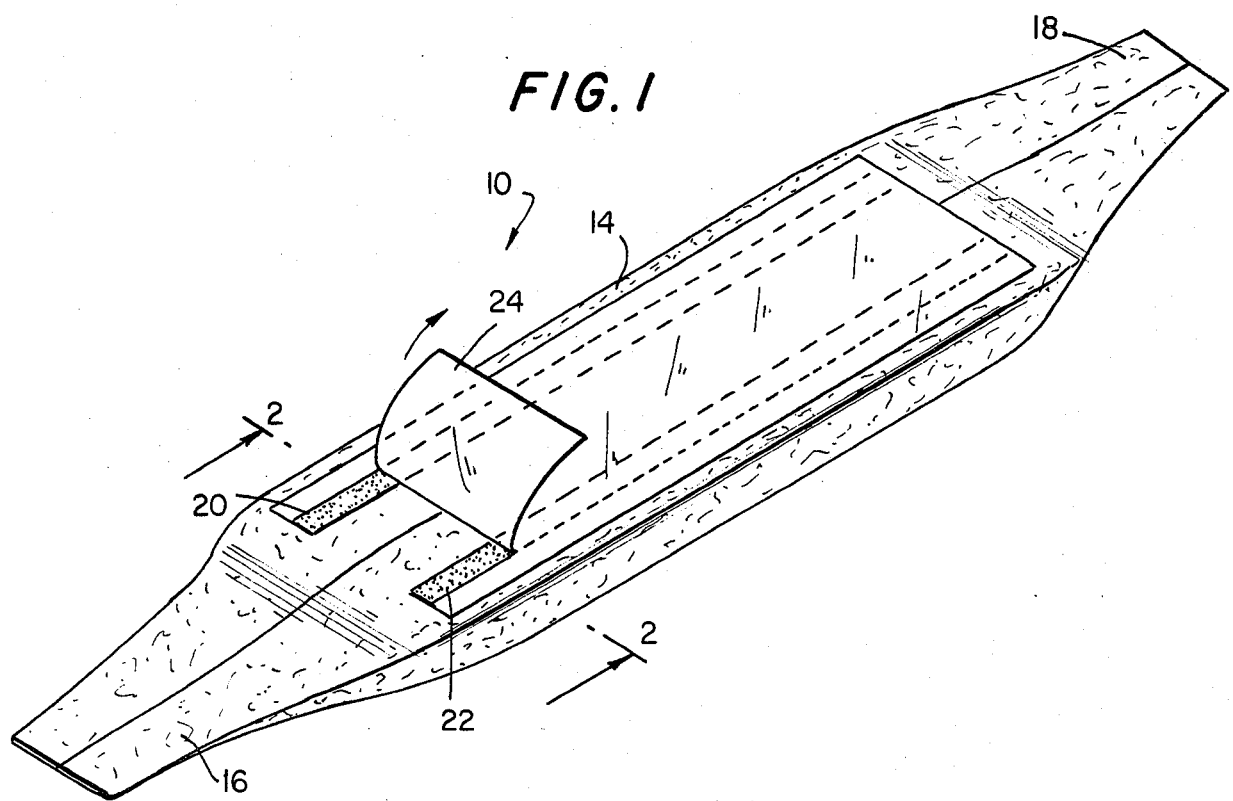
FIG. 1 is a perspective view of a sanitary napkin assembly according to the invention.

With continuing reference to the accompanying drawing, wherein like reference numerals designate similar parts throughout the various views, reference numeral 10 generally designates a sanitary pad assembly according to the present invention. The sanitary pad 10 includes an absorbent pad 12 provided with a wrapping 14 of gauze or cheese-cloth or the like and provided with the usual end tabs for securement to a conventional sanitary napkin waist belt.

Secured to the wrapping 14 by adhesive are mounting means in the form of spaced strips 20 and 22. These strips are normally covered by a peelable strip 24 in the form of an imperforate waterproof sheet of polyethylene film.

Instead of strips 20 and 22, a thin sheet of material such as sheet polyethylene may be used having a coating on both faces of an adhesive and having a plurality of openings 28 therethrough.

Figure 2:
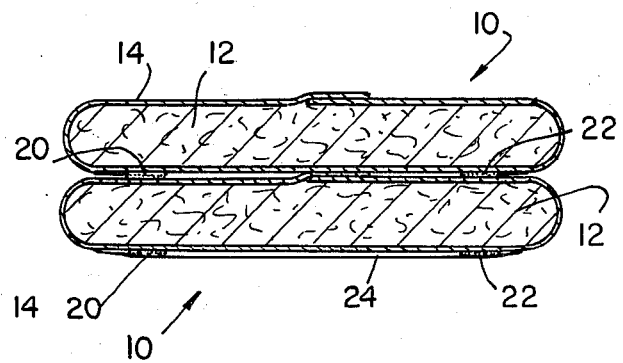
FIG. 2 is a vertical sectional view taken along line 2—2 in FIG. 1.
Figure 3:
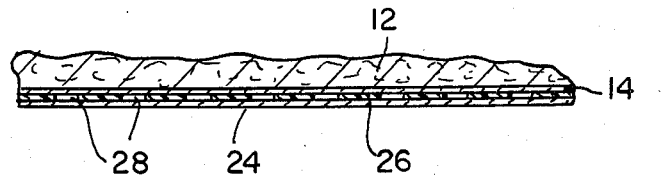
FIG. 3 is a view similar to FIG. 2 of a further preferred form of the invention.

On heavy menstral days, as shown in FIG. 2, the peelable strip 24 is removed and another sanitary napkin assembly 10 is bonded to the strips 20 and 22 by their adhesive coatings so that two sanitary napkins can now absorb the fluid. Of course, three or more sanitary napkins or the like can be used in this manner if found necessary or desirable and each absorbent pad can be comparatively thin and lightweight thus providing for the inexpensive purchase of a sanitary pad assembly usable for all conditions of mentral flow.

What is claimed is:

1. A sanitary napkin assembly comprising an absorbent pad, means secured to said absorbent pad for attaching the sanitary napkin assembly to a waistband, mounting means comprising a first thin sheet having a plurality of spaced openings therein, adhesive means coated on both sides of said first sheet, said adhesive means on one side of said first sheet fixedly attaching said first sheet to said absorbent pad, a second thin sheet of an imperforate waterproof material removably secured to said first sheet by said adhesive means on the other side of said thin sheet so that when said second sheet is peeled from said first sheet, an absorbent pad can be adhesively secured below said first recited absorbent pad.

2. A sanitary napkin assembly according to claim 1, wherein said first sheet conforms to the contours of said first absorbent pad.

3. A sanitary napkin assembly according to claim 1, wherein said second absorbent pad is affixed to the adhesive means on said other side of said first strip so that fluid from said first strip passes through said first openings into said second absorbent pad.

* * * * *